United States Patent

Pendley et al.

Patent Number: 5,185,922
Date of Patent: Feb. 16, 1993

[54] METHOD OF MAKING SUBMICROMETER MICROELECTRODES

[75] Inventors: Bradford D. Pendley; Hector D. Abruna, both of Ithaca, N.Y.

[73] Assignee: Cornell Research Foundation, Inc., Ithaca, N.Y.

[21] Appl. No.: 568,852

[22] Filed: Aug. 17, 1990

[51] Int. Cl.$^5$ .......................................... H01R 43/00
[52] U.S. Cl. ...................................... 29/825; 29/874; 65/59.25; 65/59.26; 65/59.27; 65/105; 65/DIG. 6
[58] Field of Search .................. 29/825, 874; 65/59.25, 65/105, 59.26, 59.28, 59.27, 59.32, DIG. 6

[56] References Cited

U.S. PATENT DOCUMENTS

| | | |
|---|---|---|
| 2,608,722 | 9/1952 | Stuetzer . |
| 3,282,817 | 11/1966 | Riseman et al. .................. 65/105 X |
| 3,304,165 | 2/1967 | Goto et al. ........................ 65/105 X |
| 3,498,771 | 3/1970 | Bird et al. . |
| 3,988,741 | 10/1976 | Rossopoulos . |
| 4,530,712 | 7/1985 | Kopf . |
| 4,661,236 | 4/1987 | Gelo et al. ........................ 29/825 X |
| 4,818,266 | 4/1989 | Sachs et al. . |

OTHER PUBLICATIONS

Med. & Biol. Eng vol. 10 pp. 510-515 (1972) by W. R. Levick.
Johnson et al, "A Simplified Technique for Microelectrocoagulation", Feb. 26, 1951, Science, vol. 112 pp. 182-183.
Ballintijn, "Fine Tipped Metal Microelectrodes with Glass Insulation", Apr. 1961, pp. 522-523.
Silver, "Some Observations on the Cerebral Cortex with an Ultramicro, Membrane-covered, Oxygen Electrode", May 1965, pp. 377-387.
Whalen et al, "A Microelectrode for Measuring Intracellular PO2", J. Appl. Physiol., 1967, pp. 798-801.
Meulemans et al, "Micro Carbon Electrode for Intracellular Voltametry", Anal. Chem., 1986, pp. 2088-2091.
Kim et al, "Carbon-Ring Electrodes with 1-um Tip Diameter", Anal. Chem., 1986, pp. 1782-1786.
Penner et al, "Preparation and Electrochemical Characterization of Conical and Hemispherical Ultramicroelectrodes", Anal. Chem., 1984, pp. 1630-1636.

*Primary Examiner*—Carl J. Arbes
*Attorney, Agent, or Firm*—Jones, Tullar & Cooper

[57] ABSTRACT

Microelectrodes and methods for making the same are disclosed which have electrode tip diameter of less than 10 μm. The microelectrodes include a tapered electrode wire sealed in, and surrounded by, a tapered insulator tube. In one preferred embodiment, an annealed platinum wire approximately 75 μm in diameter is inserted in an insulator tube, such as a borosilicate pipette, having an inner diameter of approximatley 600 μm. The pipette is heated to the softening temperature of borosilicate and drawn using a conventional pulling technique. As the inner diameter of the pipette draws down, it engages the annealed platinum wire and causes the wire to also draw down in diameter. Careful selection of the relative diameters of the pipette and the platinum wire ensure that the two will break at essentially the same time thereby forming a microelectrode having a platinum disk electrode of less than 10 μm diameter. Other metals, including gold, copper, silver, rhodium, iridium, tungsten and molybdenum can be used for the electrode wire.

9 Claims, 1 Drawing Sheet

METHOD OF MAKING SUBMICROMETER MICROELECTRODES

BACKGROUND OF THE INVENTION

This invention was made with Government support under Grant No. CHE-8605097, awarded by the National Science Foundation. The Government has certain rights in the invention.

The present invention relates in general to submicrometer diameter microelectrodes for use in sensors, and in biological and electrochemical experiments, and a method for making the same.

Microelectrodes possess a number of unique advantages which make them attractive for electrochemical measurements. In particular, they provide an enhanced rate of mass transport which results in a steady state current response at sufficiently slow sweep rates and reduced capacitive charging current which allows increased temporal resolution of electrochemical experiments. In addition, the small currents produced at microelectrodes lead to a reduction in the voltage drop so that electrochemical measurements in highly resistive media can be performed. Also, an improved faradaic to non-faradaic current ratio enhances the signal to noise ratio. Finally, extremely small environments can be examined with microelectrodes whose total tip size is on the order of a few micrometers. For example, these small electrodes can be used for electroanalysis in single cells.

Microelectrodes are constructed of a centrally disposed conductor which is surrounded by an insulator and has an exposed tip that acts as the electrode surface. The size of the microelectrode is therefore determined by the diameter of the conductor. The smallest diameter conductors that can be made using modern technology are on the order of one micrometer in diameter and special techniques have to be employed to make them. A variety of approaches for the construction of microelectrodes have been employed in the past and typically require that the conductor, which can be formed from platinum, carbon, tungsten or gold, for example, be electropolished or etched at its tip to reduce the tip diameter. After this, the conductors are sealed in glass pipettes or dipped in lacquer. Although these procedures can yield electrodes with diameters of several micrometers or less, in most cases the construction process is quite difficult and the success rate low.

What is needed then is a new process by which microelectrodes having electrode diameters of several micrometers or less can be formed in a fast and reliable manner without the requirement of difficult electropolishing or etching steps.

SUMMARY OF THE INVENTION

It is therefore the object of the present invention to provide a method for manufacturing micrometer and submicrometer diameter microelectrodes which does not require any complicated and unreliable electropolishing or etching steps.

It is another object of the present invention to provide a novel microelectrode structure which can be easily produced.

These and other objects of the invention are achieved by employing a tube of insulating material, such as a glass pipette, as an insulator sleeve for the microelectrode, inserting a thin ductile metal electrode wire into the tube and then subjecting the tube and the metal wire to a pulling process. This process draws both the tube and the wire down to a micrometer range diameter at which point they both break thereby forming a microelectrode tip. The resulting microelectrode structure includes a tapered electrode or wire which is sealed in intimate contact with a tapered outer insulator tube.

In one preferred form of the invention, a platinum electrode wire is employed in conjunction with a borosilicate tube or pipette. Since the borosilicate has a softening temperature that is much lower than that of platinum, the platinum wire must first be annealed so that it will become ductile at the drawing temperature of the borosilicate. The platinum wire is first inserted into the borosilicate tube which has an initial inner diameter that is substantially larger than that of the platinum wire so that the wire can easily be inserted therein. To ensure that the platinum wire will stay in position in the tube during the drawing process, the end of the wire is bent over the top end of the tube. The tube is then inserted into a conventional pipette puller which heats the temperature of the tube to its softening temperature and applies a constant tension to the tube to cause it to slowly draw down in diameter. As the tube draws down, it grips onto the annealed platinum wire and causes the wire to also draw down in diameter. With proper selection of the glass tube and platinum wire initial diameters, the drawing procedure continues until both the wire and the tube break at essentially the same time. In the process, a micrometer or submicrometer diameter microelectrode tip is formed at the point where the tube and wire break.

This procedure can be used with other types of materials with similar results. For example, the platinum wire can be replaced with a gold wire that does not have to be annealed since gold is already ductile enough to be drawable at the glass softening temperature. As long as the insulating tube and electrode wire are made of materials which draw at the same temperature, and as long as the relative diameters of the tube and wire are chosen so that they will break at essentially the same time during the drawing process, the present invention can be employed to make microelectrodes from many desired materials.

BRIEF DESCRIPTION OF THE DRAWINGS

The foregoing and additional objects, features and advantages of the present invention will become apparent from the following detailed description of preferred embodiments thereof, taken in conjunction with the accompanying drawings in which.

DETAILED DESCRIPTION OF THE PREFERRED EMBODIMENTS

Turning now to a more detailed consideration of the present invention, FIGS. 1A-D illustrate the steps employed to form a micrometer and submicrometer range diameter microelectrode in accordance with the present invention. More particularly, in FIG. 1A, a thin electrode wire 10 is inserted into a hollow tube 12, which can be a glass pipette for example, and a top end 13 of the wire 10 is bent over a top end 14 of the tube 12 to retain the wire therein. The wire 10 can be formed from any suitable ductile metal, and is preferably formed from annealed platinum. However, other metals such as gold, silver, copper, tungsten, molybdenum, iridium and rhodium can be employed depending on the desired electrode characteristics. The tube 12 can be formed from any suitable insulating material that can be drawn when heated, such as borosilicate glass.

To obtain a microelectrode diameter of less than 10 $\mu$m, the initial diameter of the wire 10 is chosen to be approximately 75 $\mu$m. As will be discussed in greater detail below, the inner diameter of the tube 12 is chosen to be substantially larger than the diameter of the wire 10 which permits easy insertion of the wire 10 into the tube 12, but more importantly results in the desired pulling action of the tube and wire as discussed below.

Figure 1A:
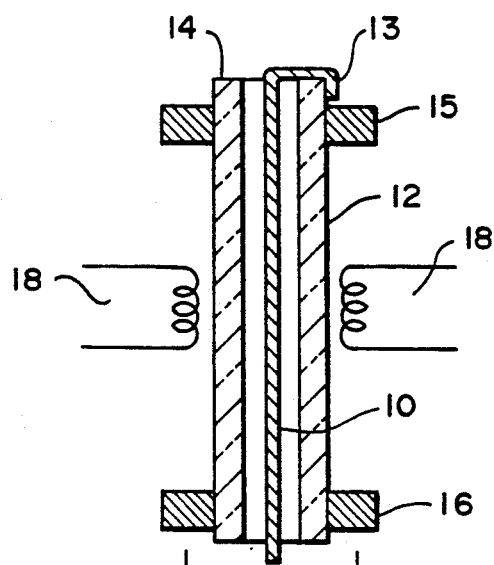
FIGS. 1A-D are diagrammatic illustrations showing the steps employed in forming a microelectrode in accordance with the process of the present invention; and, FIG. 2 is a partial perspective illustration of a microelectrode formed in accordance with the present invention.
Figure 1B:
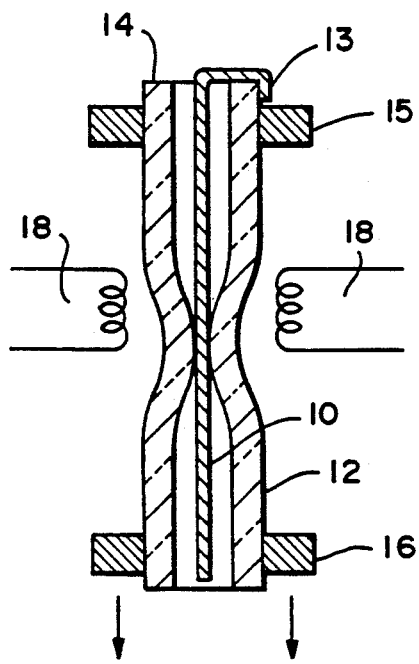
Figure 1C:
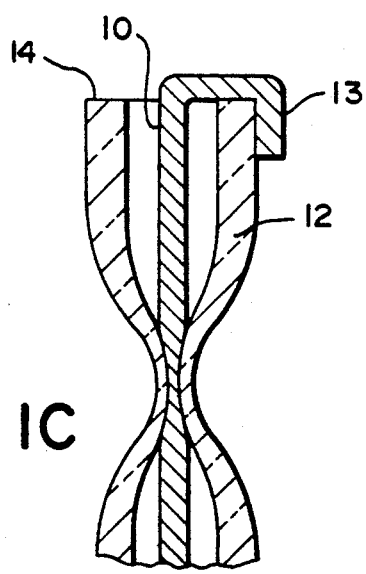

As diagrammatically illustrated in FIG. 1A, the tube 12 is clamped by means of a pair of chucks 15 and 16 of a conventional glass microelectrode puller (not shown), such as the model PE-2M puller available from the Narishige Company of Japan. It is important to note that the puller chucks 15 and 16 are attached to the tube 12 but not to the wire 10 which is initially suspended in the tube 12 by the bent over top end 13. A plurality of heating coils 18 are adjustably positioned around the outer periphery of the portion of the tube 12 which is to be softened and drawn out to form a microelectrode tip. The coils 18 heat the pipette 12 just above its softening point so that it will become ductile and can be drawn. In the case of borosilicate glass, the softening temperature is between approximately 720° and 820° C. A constant tension is applied to the bottom puller chuck 16 which causes the tube 12 to draw down until it engages the wire 10 as illustrated in FIG. 1B thereby causing the two to contact each other in a sealing manner. At this point, the pulling force on the tube 12 is transmitted to the wire 10 which also begins to draw down as illustrated in FIG. 1C. In the case of platinum wire, this drawing down can only occur if the platinum wire is first annealed. This is because platinum is not normally a ductile metal except very near its melting temperature which is approximately 1700° C. and is much higher than the softening temperature of the borosilicate glass of the tube 12.

Figure 1D:
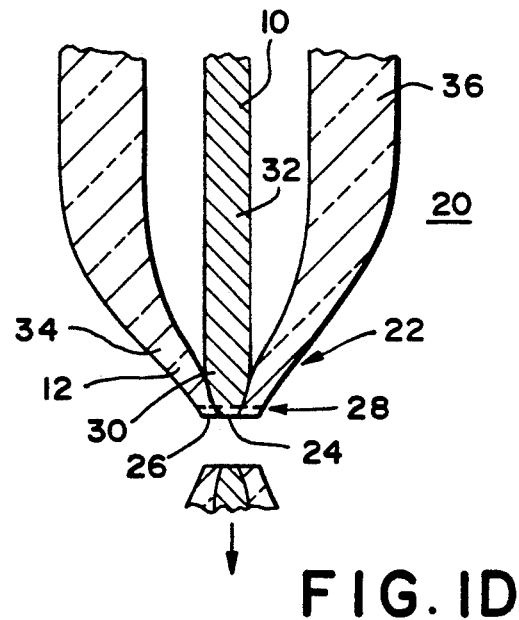
Figure 2:
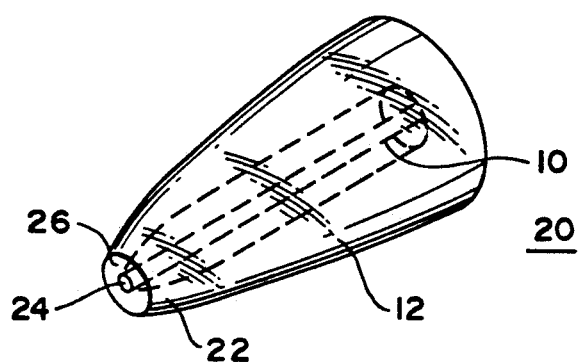

The pulling operation is continued until the wire 10 and tube 12 break at essentially the same time as illustrated in FIG. 1D. As a result as best illustrated in FIG. 2, an insulated microelectrode 20 is formed which tapers to a tip end 22 including a disk shaped electrode 24 surrounded by a tip end 26 of the tapered glass insulator tube 12. It should be noted that although the microelectrode tip end 22 can be formed solely by the breaking of the tube and wire assembly during the pulling operation, a small portion of the tip end 22 can be broken or snapped off by any suitable breaking or snapping means as indicated by the dashed lines 28 in FIG. 1D to provide a smoother electrode surface than is obtained when the wire 10 breaks during the pulling operation. Although this breaking operation results in the disk electrode 24 having a slightly larger diameter, electrodes with diameters less than 5 $\mu$m can still be obtained with this method.

As a result of the pulling operation and as also illustrated in FIG. 1D, the electrode wire 10 of the microelectrode 20 includes a first tapered portion 30 ending at the exposed electrode 24 at the tip end 22, and a second portion 32 of relatively constant diameter. Similarly, the glass tube 12 includes a first tapered portion 34 ending at the tip end 26 of the tube 12 and a second portion 36 of relatively constant diameter.

The relative diameters of the wire 10 and tube 12 must be chosen carefully to ensure that the microelectrode 20 will be properly formed. In particular, if the inner diameter of the tube 12 is too large, it will have to be drawn down too far before it contacts the wire 10 and will break before the wire 10 is drawn down to a desired diameter. On the other hand, if the inner diameter of the tube 12 is too small, it will contact the wire 10 too soon during the drawing process and cause the wire to be pulled to the breaking point before the tube 12 reaches its breaking point.

Clearly then the relative diameters of the wire 10 and tube 12 must be chosen based on the ductility of the material used for the wire 10 and the softening temperature and thickness of the tube 12. Experiments were conducted to form a platinum microelectrode in accordance with the present invention having a borosilicate glass insulator tube. Good results were obtained with an annealed platinum wire having a diameter of 75 $\mu$m and a borosilicate tube having an outer diameter of approximately 1300 $\mu$m and an inner diameter of approximately 610 $\mu$m. The heating and pulling process resulted in the formation of tapered microelectrodes having total outer diameters between 1 and 5 $\mu$m and a platinum disk electrode diameter between 0.5 and 1.5 $\mu$m.

Other experiments with the 75 $\mu$m annealed platinum wire were conducted with tubes or pipettes having inner diameters between 1000 and 1400 $\mu$m, however, these were too large for the reasons discussed above and the glass broke too early. Similarly, an experiment with a tube having an inner diameter of approximately 270 $\mu$m resulted in the platinum wire breaking before the glass. The preferred range of inner diameters for the insulator tube when employed with a 75 $\mu$m annealed platinum wire therefore appears to between 400 and 800 $\mu$m.

In yet another experiment with a 75 $\mu$m diameter gold wire, which is naturally ductile and therefore does not require annealing, good results were obtained with a tube or pipette having an outer diameter of approximately 1100 $\mu$m and an inner diameter of approximately 270 $\mu$m. This is in contrast to the same experiment discussed above with the 75 $\mu$m annealed platinum wire, and can be explained by the fact that the ductility of the gold wire differs from that of the annealed platinum wire so that the gold wire stretches more than the platinum wire. The preferred range of inner diameters for the insulator tube when employed with a 75 $\mu$m gold wire therefore appears to be somewhere between 200 and 500 $\mu$m.

The key to the process of the present invention is therefore to choose the materials for the electrode wire and insulator tube so that they can both be pulled at the same temperature without either of them melting or in the alternative cracking, and to then choose the relative diameters of the tube and the electrode wire so that the wire will be pulled just enough to cause both the wire and the tube to break at essentially the same time.

This process of microelectrode fabrication offers a number of significant advantages over prior art microelectrode fabrication techniques. First, it is extremely quick and easy to fabricate electrodes with this process. Also, it allows for the construction of very small microelectrodes less than 10 $\mu$m in total tip diameter with smooth tapers of the wire electrode and insulator tube and a superior seal between the two. Further, this procedure has a better success rate over many of the prior techniques. Finally, although measurement equipment does not exist which can accurately measure such small dimensions in this environment, this fabrication procedure has resulted in the formation of a platinum disk microelectrode having a diameter estimated to be less than 100 angstroms which represents the smallest platinum disk electrode ever reported and further illustrates the capability of this fabrication process.

Although the invention has been disclosed in terms of preferred embodiments, it will be understood that numerous variations and modifications could be made thereto without departing from the true spirit and scope thereof as defined in the following claims. For example, it is possible that a conventional platinum wire could be employed in place of the annealed platinum wire if the borosilicate glass tube were replaced with a tube formed from a material having a softening temperature near the melting temperature of platinum, such as quartz.

We claim:

1. A method for fabricating microelectrodes comprising the steps of:
    a) selecting a hollow tube of insulating material which becomes ductile at a softening temperature and has an inner diameter and an outer diameter;
    b) selecting an electrode wire formed of ductile conductive material having a melting temperature above the softening temperature of said hollow tube, said electrode wire having an outer diameter substantially smaller than the inner diameter of said tube;
    c) inserting said electrode wire into said tube;
    d) heating said tube to its softening temperature and simultaneously applying tension to said tube to cause it to draw down in diameter into sealing contact with said electrode wire, thereby causing said electrode wire to also be drawn down in diameter; and,
    e) continuing to apply tension to said tube until said tube and electrode wire break and thereby form a microelectrode having a tip end at the point where said tube and electrode wire break.

2. The method of claim 1 wherein the step of selecting an electrode wire comprises selecting an electrode wire formed of a metal selected from the group consisting of platinum, gold, copper, silver, rhodium, iridium, tungsten and molybdenum.

3. The method of claim 2 wherein the step of selecting a tube comprises selecting a tube formed from borosilicate glass.

4. The method of claim 1 further including the step of suspending said electrode wire in said tube after it is inserted in said tube by bending a top end of said wire over a top end of said tube.

5. The method of claim 1 further including the step of selecting the inner diameter of the tube and the outer diameter of the electrode wire so that both the tube and the wire will break at essentially the same time when drawn.

6. The method of claim 5, wherein the step of selecting a tube comprises selecting a tube formed from borosilicate glass, the step of selecting an electrode wire comprises selecting an annealed platinum wire, and the step of selecting the inner diameter of the tube and the outer diameter of the electrode wire comprises selecting the inner diameter of the tube to be between 400 and 800 $\mu$m and the outer diameter of the electrode wire to be approximately 75 $\mu$m.

7. The method of claim 5, wherein the step of selecting a tube comprises selecting a tube from borosilicate glass, the step of selecting an electrode wire comprises selecting a gold wire, and the step of selecting the inner diameter of the tube and the outer diameter of the electrode wire comprises selecting the inner diameter of the tube to be between 200 and 500 $\mu$m and the diameter of the electrode wire to be approximately 75 $\mu$m.

8. The method of claim 1, further including the step of breaking off a small portion of said tube and electrode wire adjacent said microelectrode tip end to form a new microelectrode tip end.

9. The method of claim 1, wherein the step of selecting an electrode wire comprises selecting a electrode wire formed from material selected from the group consisting of gold and annealed platinum and having a diameter of approximately 75 $\mu$m so that the electrode wire will be drawn down to a diameter less than 10 $\mu$m before it breaks.

* * * * *